United States Patent [19]

Hörold et al.

[11] Patent Number: 6,090,967
[45] Date of Patent: Jul. 18, 2000

[54] PROCESS FOR PREPARING PHOSPHONOUS ESTERS

[75] Inventors: Sebastian Hörold, Erftstadt; Norbert Weferling; Heinz-Peter Breuer, both of Hürth, all of Germany

[73] Assignee: Clariant GmbH, Frankfurt, Germany

[21] Appl. No.: 09/342,771

[22] Filed: Jun. 29, 1999

[30] Foreign Application Priority Data

Jun. 29, 1998 [DE] Germany .......................... 198 28 861

[51] Int. Cl.⁷ ..................................... C07F 9/28
[52] U.S. Cl. .................. 558/105; 524/133; 558/108; 558/110; 558/177
[58] Field of Search ................... 558/105, 108, 558/110, 177

[56] References Cited

U.S. PATENT DOCUMENTS 6,011,172  1/2000  Weferling et al. ........................ 562/8

*Primary Examiner*—Michael G. Ambrose
*Attorney, Agent, or Firm*—Scott E. Hanf

[57] ABSTRACT

The present invention relates to a process for preparing phosphonous esters which comprises a) reacting elemental yellow phosphorus with alkyl halides in the presence of alkali metal hydroxides and/or alkaline earth metal hydroxides to form a mixture which comprises, as main components, the alkali metal salts and/or alkaline earth metal salts of the alkylphosphonous, phosphorous and hypophosphorous acids, b) removing the alkylphosphonous acid from the mixture obtained by a)

c) esterifying the alkylphosphonous acid.

The invention likewise relates to the use of the phosphonous esters prepared by this process.

16 Claims, No Drawings

PROCESS FOR PREPARING PHOSPHONOUS ESTERS

BACKGROUND OF THE INVENTION

Phosphonous acids and their esters are valuable synthesis building blocks for preparing polymers and plastics. The phosphinic acids and phosphinic esters which are accessible from phosphonous acids and their esters can be used as comonomers in the preparation of polyesters. In this manner, low-flammability polyesters are obtained, which polyesters can be processed to form fibers, for example.

According to DE-A 21 00 779, dialkyl dialkylphosphinates are obtained by adding phosphonous esters to olefins using free-radical initiators.

DE 25 40 283 A1 describes the addition of phosphines to α, β-unsaturated carboxylic acids in the presence of aqueous hydrochloric acid and subsequent oxidation.

Phosphonous monoesters can be obtained by esterifying phosphonous acids. Ethylene oxide, for example, can be used for the esterification (Houben-Weyl, Volume 12/1, p. 320).

In addition, phosphonous monoesters are accessible from phosphonous diesters by saponification or from phosphonous dihalides by reaction with alcohols (Houben-Weyl, Volume 12/1, p. 320). Usually, the phosphonous diesters are prepared from phosphonous dihalides.

The abovementioned phosphonous dihalides, eg. methyldichlorophosphine, which can be used as starting materials for other syntheses, have themselves been prepared to date in a complex synthesis from phosphorus trihalides and alkyl halides in the presence of aluminum chloride (Houben-Weyl, Volume 12/1, p. 306). The reaction is highly exothermic and can be controlled only with difficulty industrially. In addition, various byproducts are formed which are, as are also some of the abovementioned starting products, toxic and/or corrosive, and therefore highly undesirable.

The abovementioned processes are, in addition, complex and cannot be carried out on an industrial scale without difficulty.

There is therefore a requirement for a process for preparing functional phosphonous esters, which process can be carried out in a simple manner and in which uniform products are obtained in high yield. A process of this type should also be clearly superior environmentally to those known hitherto.

SUMMARY OF THE INVENTION

The present invention relates to a process for preparing phosphonous esters.

The object thus underlying the invention is to provide a process for preparing phosphonous esters, which process avoids the abovementioned disadvantages and starts from elemental yellow phosphorus as starting material. In addition, the synthesis is to start from readily accessible products and be particularly economical.

This object is achieved by a process of the type described at the outset which comprises a) reacting elemental yellow phosphorus with alkyl halides in the presence of alkali metal hydroxides and/or alkaline earth metal hydroxides to form a mixture which comprises, as main components, the alkali metal salts and/or alkaline earth metal salts of the alkylphosphonous, phosphorous and hypophosphorous acids, b) removing the alkylphosphonous acid from the mixture obtained by a)

c) esterifying the alkylphosphonous acid.

DESCRIPTION OF THE PREFERRED EMBODIMENTS

Preferably, the alkyl halides are methyl chloride or methyl bromide.

Preferably, the reaction in step a) is carried out in a two-phase system of aqueous alkali metal hydroxide or alkaline earth metal hydroxide or mixtures thereof and an organic solvent.

Preferably, as organic solvent, use is made of unbranched or branched alkanes, alkyl-substituted aromatic solvents, water-immiscible, or only partially water-miscible, alcohols or ethers, alone or in combination with one another.

Particularly preferably, as organic solvent, use is made of toluene, alone or in combination with alcohols.

Preferably, the reaction is carried out in the presence of a phase-transfer catalyst.

Preferably, the phase-transfer catalyst is tetraalkylphosphonium halides, triphenylalkylphosphonium halides or tetraorganylammonium halides.

Preferably, the temperature in the reaction is −20 to +60° C.

Particularly preferably, the temperature is 0 to 30° C.

Preferably, the reaction is carried out at a pressure of 0 to 10 bar.

Preferably, the process according to the invention is carried out in such a manner that the yellow phosphorus is suspended in a solvent or in a solvent mixture and is then reacted with alkyl halide and a compound of the formula MOH or M'(OH)$_2$ or mixtures thereof, where M is an alkali metal and M' is an alkaline earth metal.

Preferably, the yellow phosphorus and the alkyl halide are reacted with one another in a molar ratio of 1:1 to 1:3, the molar ratio of yellow phosphorus to the compound of the formula MOH or M' (OH)$_2$ being 1:1 to 1:5.

Preferably, in step b), the alkylphosphonous acid is removed by distillation.

Preferably, in step c), esterification is carried out by ethoxylation.

Preferably, for the ethoxylation according to step c), use is made of an oxirane such as ethylene oxide, propylene oxide or long-chain oxiranes. Alternatively, ethylene carbonate can also be used. However, esterification can also be carried out directly using an alcohol with elimination of water.

The phosphonous acid can be esterified to give the corresponding monoester by, for example, reaction with higher-boiling alcohols with removal by azeotropic distillation of the water formed.

Suitable alcohols are, for example, butanol, hexanol, octanol, ethyl hexanol, ethylene glycol, diethylene glycol and/or glycerol.

Preferably, the alkylphosphonous acid is methanephosphonous acid.

The invention also relates to the use of the phosphonous esters prepared by the process according to the invention as reactive flame retardants for polymers.

The invention also relates to the use of the phosphonous esters prepared by the process according to the invention as reactive flame retardants for thermoplastic polymers such as polyethylene terephthalate, polybutylene terephthalate or polyamide.

The invention also relates to the use of the phosphonous esters prepared by the process according to the invention as reactive flame retardants for thermosetting resins such as unsaturated polyester resins, epoxy resins, polyurethanes or acrylates.

The invention also relates to the use of the phosphonous esters prepared by the process according to the invention as precursor for the synthesis of phosphorous compounds.

The invention is illustrated by the examples below:

Example 1

Reaction of Yellow Phosphorus with Alkyl Halide

A 5 l stainless steel pressure reactor is charged with 2 l of toluene in which 25 g (0.05 mol) of tributylhexadecylphosphonium bromide have previously been dissolved and the solution is preheated to 60° C. 62 g (2 mol) of molten yellow phosphorus are introduced into the reactor, cooled to 0° C. with vigorous stirring and then 202 g (4 mol) of methyl chloride are condensed in. Within the course of 1 h, 1000 g of a solution of 600 g of KOH in 400 g of water are then introduced, the temperature in this case being kept at 0° C. and the reaction being continued for a further 1 h at this temperature. The product mixture is heated to room temperature, diluted with 400 ml of water and the reactor is then expanded via a combustion stage. Two phases are obtained. The aqueous phase comprises 64.2 mol % of methanephosphonous acid in the form of its potassium salt. After neutralization with hydrochloric acid, the methanephosphonous acid is distilled off in vacuo.

A yellow liquid is obtained. $^{31}$P-NMR (CHCl$_3$): 58 ppm

Example 2

Ethoxylation of Methanephosphonous Acid

A 500 ml five neck flask equipped with gas inlet tube, thermometer, intensive agitator and reflux condenser with gas combustion is charged with 80.3 g (1 mol) of methanephosphonous acid. Ethylene oxide is introduced at room temperature. A reaction temperature of 70° C. is established with cooling. After completion of ethylene oxide uptake, reaction is continued for a further hour at 80° C. The ethylene oxide uptake is 65.7 g, equivalent to 1.5 mol. The acid number of the product is less than 1 mg of KOH/g. A colorless, water-white product is obtained. $^{31}$P-NMR: 38 ppm.

What is claimed is:

1. A process for preparing phosphonous esters which comprises d) reacting elemental yellow phosphorus with alkyl halides in the presence of alkali metal hydroxides and/or alkaline earth metal hydroxides to form a mixture which comprises, as main components, the alkali metal salts and/or alkaline earth metal salts of the alkylphosphonous, phosphorous and hypophosphorous acids, e) removing the alkylphosphonous acid from the mixture obtained by a) and f) esterifying the alkylphosphonous acid.

2. The process as claimed in claim 1, wherein the alkyl halides are methyl chloride or methyl bromide.

3. The process as claimed in claim 1, wherein the reaction is carried out in an organic solvent.

4. The process as claimed in claim 3, wherein the organic solvent is selected from unbranched or branched alkanes, alkyl-substituted aromatic solvents, water-immiscible, or only partially water-miscible, alcohols or ethers, alone or in combination with one another.

5. The process as claimed in claim 4, wherein the organic solvent is toluene, alone or in combination with alcohols.

6. The process as claimed in claim 1, wherein the reaction is carried out in the presence of a phase-transfer catalyst.

7. The process as claimed in claim 6, wherein the phase-transfer catalyst is selected from tetraalkylphosphonium halides, triphenylalkylphosphonium halides or tetraorganylammonium halides.

8. The process as claimed in claim 1, wherein the temperature in the reaction is −20 to 60° C.

9. The process as claimed in claim 8, wherein the temperature is 0 to 30° C.

10. The process as claimed in claim 1, wherein the reaction is carried out at a pressure of 0 to 10 bar.

11. The process as claimed in claim 1, wherein the yellow phosphorus is suspended in a solvent or in a solvent mixture and is then reacted with an alkyl halide and a compound of the formula MOH or M'(OH)$_2$ or mixtures thereof, where M is an alkali metal and M' is an alkaline earth metal.

12. The process as claimed in claim 1, wherein the yellow phosphorus and the alkyl halide are reacted with one another in a molar ratio of 1:1 to 1:3, the molar ratio of yellow phosphorus to the compound of the formula MOH or M'(OH)$_2$ being 1:1 to 1:5.

13. The process as claimed in claim 1, wherein, in step b), the alkylphosphonous acid is removed by distillation.

14. The process as claimed in claim 1, wherein, in step c), esterification is carried out by ethoxylation.

15. The process as claimed in claim 1, wherein, in step c), esterification is carried out directly by reaction with alcohols with elimination of water.

16. The process as claimed in claim 1, wherein the phosphonous acid is methanephosphonous acid.

* * * * *